United States Patent [19]

Lehmann

[11] Patent Number: 4,711,241
[45] Date of Patent: Dec. 8, 1987

[54] SURGICAL FILAMENT COATING

[75] Inventor: Leonard T. Lehmann, Fairfield, Conn.

[73] Assignee: American Cyanamid Company, Stamford, Conn.

[21] Appl. No.: 903,799

[22] Filed: Sep. 5, 1986

[51] Int. Cl.$^4$ ............................................. A61L 17/00
[52] U.S. Cl. .............................. 128/335.5; 128/334 R; 427/2; 428/375; 428/378; 623/13
[58] Field of Search ............... 128/334 R, 335, 335.5; 260/410.6, 410.9; 560/185; 427/2; 428/378, 375; 106/243, 287.24; 623/13

[56] References Cited

U.S. PATENT DOCUMENTS

| | | | |
|---|---|---|---|
| 2,683,136 | 7/1954 | Higgins | 260/78.3 |
| 2,733,252 | 1/1956 | Thompson et al. | 260/410.9 |
| 2,789,992 | 4/1957 | Thompson et al. | 260/410.9 |
| 3,141,030 | 7/1964 | Buddemeyer | 260/410.9 |
| 3,475,204 | 10/1969 | Patterson | 117/138.8 |
| 3,636,952 | 1/1972 | George | 604/364 |
| 4,010,196 | 3/1977 | Tsuk | 260/484 A |
| 4,027,676 | 6/1977 | Mattei | 128/335.5 |
| 4,146,548 | 3/1979 | Forsythe | 260/410.6 |
| 4,185,637 | 1/1980 | Mattei | 128/335.5 |
| 4,201,216 | 5/1980 | Mattei | 128/335.5 |
| 4,300,565 | 11/1981 | Rosensaft et al. | 128/335.5 |
| 4,422,952 | 12/1983 | Koulbanis et al. | 260/410.6 X |
| 4,532,929 | 8/1985 | Mattei et al. | 128/335.5 |

Primary Examiner—R. J. Apley
Assistant Examiner—Paul B. Prebilic
Attorney, Agent, or Firm—Charles F. Costello, Jr.

[57] ABSTRACT

The invention discloses a surgical filament having a coating comprising a compound of the formula:

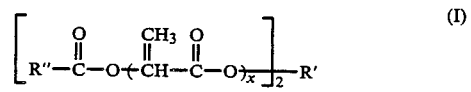

(I)

wherein x is at least 2, R' is selected from the group consisting of an alkaline-earth metal ion or radical, and R" is an alkyl group having at least 12 carbon atoms in the backbone. In a specific embodiment, the surgical filament is a bioabsorbable suture or ligature manufactured from a polymer containing at least one glycolic acid ester linkage.

1 Claim, No Drawings

SURGICAL FILAMENT COATING

BACKGROUND AND SUMMARY OF THE INVENTION

This invention relates to a surgical filament having a coating. The coating comprises a compound of the formula:

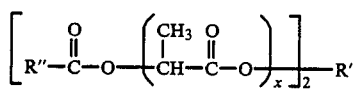

wherein x is at least 2, R' is selected from the group consisting of an alkaline-earth metal ion or radical, and R" is an alkyl group having at least 12 carbon atoms in the backbone. In one embodiment, x is 2. In another embodiment, x is at least 4. In a specific embodiment R' is an alkaline-earth metal ion. In a more specific embodiment, the ion is selected from the group consisting of magnesium, calcium, barium, and zinc.

A surgical filament having in combination a bioabsorbable suture or ligature, and a coating has also been invented. The coating comprises a compound of the formula:

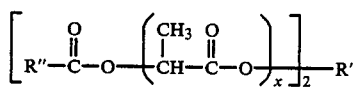

wherein x is at least 2, R' is selected from the group consisting of an alkaline-earth metal ion or radical, and R" is an alkyl group having from about 12 to 22 carbon atoms in the backbone. In one embodiment, the bioabsorbable suture or ligature is manufactured from a synthetic polymer.

In a specific embodiment, the polymer is manufactured from at least one monomer selected from the group consisting of lactides, 1,4-dioxane-2,3-dione and 1,3-dioxan-2-one.

In another embodiment, the weight of the coating on the suture or ligature is from about 0.5 to 5.0 percent based on the weight of the filament. In a further embodiment, x is 2 and R is calcium.

Finally, a surgical filament comprising in combination a bioabsorbable suture or ligature manufactured from a polymer containing at least one glycolic acid ester linkage, and a coating has been invented. The coating comprises a compound of the formula:

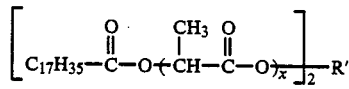

wherein x is at least 2 and R' is an alkaline-earth metal ion. In one embodiment, the polymer is a homopolymer. In another embodiment, the polymer is a copolymer. In a specific embodiment, the copolymer contains at least one trimethylene carbonate linkage.

In still another embodiment the filament is braided. In a further embodiment, the weight of the coating on the braided suture or ligature is from about 1.5 to 3.0 percent based on the weight of the filament.

DESCRIPTION OF PREFERRED EMBODIMENT

A coating composition of this invention can be applied to any suture material to improve its fiber lubricity. It is useful, for example, to improve a suture tie-down characteristic.

Specifically, a coating composition of this invention is useful with a synthetic bioabsorbable multifilament suture. The bioabsorbable suture can be composed of a homopolymer or copolymer containing at least one glycolic acid ester linkage.

All or a portion of the coating composition of this invention comprises a compound of the formula:

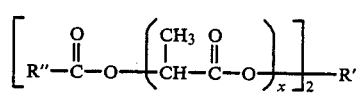

wherein x is at least 2, R' is selected from the group consisting of an alkaline-earth metal ion or radical, and R" is an alkyl group having at least 6 carbon atoms in the backbone. An ester of R" having from about 12 to 22 carbon atoms, and mixtures thereof, are preferred.

A compound of formula (I) can be prepared by methods known in the prior art e.g., see U.S. Pat. Nos. 4,146,548; 4,010,196; 2,733,252; and Symposium on Oils And Fats 38 38–40 (1976), which are incorporated herein by reference. See also The Merck Index, Tenth Ed., Merck & Co., NJ, 1983, Monograph No. 1682, which is also incorporated herein by reference.

Illustrative of formula (I) compounds are magnesium, barium, aluminum or zinc palmityl lactylate; and calcium, magnesium, barium, aluminum or zinc oleyl lactylate. Particularly preferred is a commercially available "food grade" of calcium stearoyl-2-lactylate, which is available, e.g., from C. J. Patterson Co., MO, U.S.A.

Illustrative of solvents useful in preparing the calcium stearoyl-2-lactylate coating composition are the aromatic series of benzene, toluene, xylene, and mesitylene, and the aliphatic solvents, 1,1,2-trichloroethane and chloroform.

A fatty acid ester coating composition of formula (I) is conveniently applied to a suture by passing the suture through a container of the coating composition. Other conventional methods of applying coatings or finishes to continuous strands of fibers may also be used with substantially similar results, e.g. melt coating. Preferably, the application of the coating to the suture is regulated to provide from about 1 to 5 percent dry coating by weight of the suture fiber.

The coating adheres well to the suture. Also, the coating is translucent so that the appearance of the coated suture is not significantly altered by the coating. Also, there is no appreciable dusting or flaking of the coating during suture tie-down.

In coating multifilament sutures with the fatty acid ester in accordance with the present invention, it is not necessary that every filament within the suture be individually or completely coated. Under most circumstances, the coating will penetrate at least partially into the interstices of the suture. What is critical is that the outer surface of the suture be well coated in order to reduce frictional forces during suture tie-down.

The amount of coating composition applied to the suture fiber, or the coating add-on, will vary depending upon the construction of the fiber. For example, the number of filaments and tightness of a braid or twist, and the nature of the coating material, e.g., its viscosity and consistency will vary the amount of coating applied to the fiber.

In general, the dry coating composition applied to a braid will constitute from about 1 to 5 percent by weight of the coated suture fiber. However, it is to be understood that coating composition add-on may range from as little as about 0.5 percent by weight to as much as about 10 percent by weight or higher in some cases.

As a practical matter, and for reasons of economy and general performance, it is preferred to apply the minimum amount of coating composition. This level of add-on can be determined without undue experimentation for any particular fiber-coating system, and is usually within the range of 2 to 4 dry weight percent, by weight of the coated suture fiber.

To achieve specific desired properties, the coating compositions of this invention can further be plasticized by various agents such as glyceryl triacetate, butyl citrate, ethyl benzoate, dibutyl phthalate, etc. Various additives can also be included in the formulation to improve the performance of the lubricants such as calcium stearate or other salts of fatty acids, and bioabsorbable polyester and polyester-carbonate salts can be used. Also, water soluble lubricants such as a poly(alkylene oxide) can be included.

The coating composition can also include a poly($\beta$-hydroxybutyrate-co-$\beta$-hydroxyvalerate) and/or a poly($\beta$-hydroxybutyrate). A polymer of ($\beta$-hydroxybutyrate) can improve the knot run-down performance of a multifilament suture. Also, a polymer of ($\beta$-hydroxybutyrate) can be used as a binder, to hold the lubricant in place on the surface of a suture. Thus the lubricant can better resist displacement caused by friction during the knotting of the suture. Finally, tests indicate that poly($\beta$-hydroxybutyrate-co-$\beta$-hydroxyvalerate), and mixtures thereof, with calcium stearoyl-2-lactylate performs well under both suture dry and wet conditions.

The improvement in suture properties imparted to a synthetic bioabsorbable suture may be determined semi-quantitatively by comparing the hand of a coated and uncoated suture during the act of tying down a single throw knot. Such a comparison can be made on both a wet and dry suture since many suture coatings show different tie-down properties when tested wet or dry. It is to be understood that the term wet tie-down refers to the testing of a coated suture in an in-vivo or in-vitro simulated fluid, and the ten day tie-down refers to bench top testing of a coated suture without exposure to an in-viro or simulated fluid.

The method and the coating of the present invention are further illustrated by the following examples.

EXAMPLE 1

Into a heated polymerization reactor was charged 45 g of glycolide, 55 g of trimethylene carbonate (TMC), 9.23 mg of $SnCl_2 \cdot 2H_2O$, and 97.21 of diethylene glycol (hereinafter abbreviated as DEG). The reaction mixture was heated with stirring under dry nitrogen at 186° C. for 75 minutes.

The resulting copolymer was discharged as a viscous melt which was cooled and ground to fine particles. The ground copolymer was dried under vacuum at 60° C. overnight.

The copolymer had a composition of 47.7 weight percent trimethylene carbonate and 52.3 weight percent of glycolide. Less than 2.5 percent of monomeric trimethylene carbonate was present. The inherent viscosity was 0.98 dl/g.

EXAMPLE 2

The copolymer of Example 1 was formulated as follows for evaluation as a coating for a braided absorbable suture:

Coating Formulation 1 (Control)

6.0 grams of copolymer
9.0 grams of Xylene
80.0 grams of Methylene Chloride

Coating Formulation 2

6.0 grams of Calcium Stearoyl-2-Lactylate (Verv TM)*
1.6 grams of copolymer
9.0 grams of Xylene
80.0 grams of Methylene Chloride
*C. J. Patterson Co., Kansas City, MO. U.S.A.

Coating Formulation 3

3.0 grams of Calcium Stearoyl Lactylate (Verv TM)
3.0 grams of Copolymer
4.5 grams of Xylene
40.2 grams of Methylene Chloride

EXAMPLE 3

A commercially available poly($\beta$-hydroxybutyrate-co-$\beta$-hydroxyvalerate) was obtained from ICI Ltd., U.K. and then placed into the following formulations:

Coating Formulation 4 (Control)

0.45 grams of polymer
0.70 grams of Xylene
6.00 grams of Methylene Chloride

Coating Formulation 5

6.0 grams of Calcium Stearoyl-2-Lactylate (Verv TM)*
1.6 grams of polymer
9.0 grams of Xylene
80.0 grams of Methylene Chloride
*C. J. Patterson Co., Kansas, MO. U.S.A.

Five 20 foot lengths of size 2/0 polyglycolic acid braid was formed into five skeins. One skein was immersed in each of the formulations 1 to 5 above for 5 minutes. The skeins were then removed, allowed to drain, and dried for 1 hour. The dried skeins were then straightened and cut into suitable lengths.

Each length was then tied around a conventional tubular rubber tying board in the following manner. A single throw was made and then run down to the tubing to assess the resistance of the knot to rebound (the ability of the single throw to remain in position after the run down is complete). A square knot was then formed and run down to the tubing to assess the stick-slipping of the knot (which is also termed chatter) as it runs down and to assess the force required to initiate and sustain the run down.

The rating system used to evaluate these coatings was:

Excellent (a) No stick-slip during run down.
(b) Moderate force required which does not result in damage to the sleeve fibers of the suture.
(c) No rebound of the single throw.

Good (a) No stick-slip during run down.
(b) Run-down force is a little high, but no damage is done to the sleeve fiber.
(c) Minor rebound of the single throw.

Fair (a) Some stick-slip during run down.
(b) Run-down force is somewhat high and minor damage to the sleeve fiber is noted.
(c) Minor rebound of the single throw can occur.

Poor (a) High stick-slip in run down.
(b) High damage or even breaking of the strand occurs.
(c) High rebound of the single throw occurs.

The suture strands coated only with the glycolide/TMC copolymer of Formulation 1 were rated between excellent and good. The suture strands coated with the mixture of Verv ™ and the glycolide/TMC copolymer of Formulation 2 were rated fair; the suture strands coated with the mixture of Formulation 3 were rated excellent. The suture strands coated with Formulations 4 and 5 were both rated between good and excellent.

EXAMPLE 4

The commercially available poly(β-hydroxybutyrate-co-β-hydroxyvalerate) of Example 3, was formulated as follows:

Coating Formulation 6

4.0 grams PHB-PHV 70/30 polymer
4.0 grams of Calcium Stearyl Lactylate
16.84 grams Xylene (19.6 cc)
175.16 grams Methylene Chloride (133.1 cc)

All liquids are added to preweighed solids and the mixture is shaken for six hours at room temperature to get solubility.

A description of the coating method for the above suture and coating formulations is as follows. A commercially available coater (e.g. from the Bouligny Co., U.S.A.) is set to operate on a filament travelling at a speed of 50 feet per minute. The circulating air in the drying oven is adjusted to be 80° C.

There is only one pass of the filament through the capillary coating apparatus, and then through the drying oven. The coating pump is adjusted to give about 5 to 8 drops per minute at the capillary apparatus.

Using the above coating method, the percent pick up was about 3.5 to 3.6 percent based on the weight of the filament. It is to be understood that this amount of pickup can be increased or decreased by any person skilled in the art without undue experimentation by adjusting the above parameters. Preferably, the amount of pick up is increased by decreasing the amount of solvent in the formulation; and vice versa.

What is claimed:

1. A surgical filament comprising in combination a bioabsorbable suture or ligature manufactured from a copolymer containing at least one glycolic acid ester and trimethylene carbonate linkage, and having on the surface thereof a coating comprising a compound of the formula:

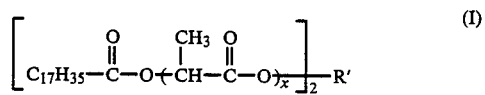

wherein x is at least 2 and R' is an alkaline-earth metal ion.

* * * * *